United States Patent
Elle et al.

(10) Patent No.: US 8,282,568 B2
(45) Date of Patent: Oct. 9, 2012

(54) METHOD FOR ESTIMATING CARDIAC PUMPING CAPACITY

(75) Inventors: Ole Jakob Elle, Olso (NO); Erik Fosse, Olso (NO); Per Steinar Halvorsen, Olso (NO)

(73) Assignee: Bio-Medisinsk Innovasjon AS, Oslo (NO)

( * ) Notice: Subject to any disclaimer, the term of this patent is extended or adjusted under 35 U.S.C. 154(b) by 1106 days.

(21) Appl. No.: 12/149,400

(22) Filed: Apr. 30, 2008

(65) Prior Publication Data

US 2008/0281214 A1  Nov. 13, 2008

Related U.S. Application Data

(60) Provisional application No. 60/914,973, filed on Apr. 30, 2007.

(51) Int. Cl.
*A61B 5/0402* (2006.01)
(52) U.S. Cl. .............................. 600/508; 600/527; 607/9
(58) Field of Classification Search .................. 600/508, 600/513, 515, 527; 607/9, 16, 17, 18
See application file for complete search history.

(56) References Cited

U.S. PATENT DOCUMENTS

| | | | |
|---|---|---|---|
| 4,947,854 A | 8/1990 | Rabinovitz et al. | |
| 5,188,106 A | 2/1993 | Nappholz et al. | |
| 5,628,777 A | 5/1997 | Moberg et al. | |
| 6,009,349 A | 12/1999 | Mouchawar et al. | |
| 6,026,324 A * | 2/2000 | Carlson | 607/27 |
| 7,139,609 B1 | 11/2006 | Min et al. | |
| 2004/0225332 A1 | 11/2004 | Gebhardt et al. | |
| 2005/0043651 A1* | 2/2005 | Elle et al. | 600/595 |
| 2007/0175827 A1* | 8/2007 | Wariar | 210/645 |

FOREIGN PATENT DOCUMENTS

| | | |
|---|---|---|
| WO | WO-95/33517 A1 | 12/1995 |
| WO | WO-03/061473 | 7/2003 |

OTHER PUBLICATIONS

Hartley et al., "Doppler measurement of myocardial thickening with a single epicardial transducer," Am. J. Physiol. 245 (Heart Circ. Physiol. 14) H1066-H1072, 1983.

(Continued)

*Primary Examiner* — Carl H Layno
*Assistant Examiner* — Pamela M Bays
(74) *Attorney, Agent, or Firm* — Birch, Stewart, Kolasch & Birch, LLP

(57) ABSTRACT

A system and a method for estimating changes in cardiac pumping capacity in response to an intervention from data recorded by an accelerometer positioned on an outer surface of the heart. Interventions such as intravenous administration of nitroprusside, betablocker, epinephrine (adrenaline), or changes in the intravascular volume such as by fluid filling, are considered. It is shown that it is possible to directly correlate changes in cardiac pumping capacity to changes in parameters or graphical representation derived from signals characteristic to the acceleration an outer surface of the heart. In particular, it is shown how the effect of the interventions can be directly read from these parameters or graphical representations, and can thereby assist in decisions regarding the treatment of a cardiac surgery patient. The invention is preferably used in a post-surgery monitoring unit for surveillance of cardiac surgery patients.

4 Claims, 15 Drawing Sheets

OTHER PUBLICATIONS

Skulstad et al., "Postsystolic Shortening in Ischemic Myocardium: Active Contraction or Passive Recoil?," Circulation, American Heart Association, 2002, pp. 718-724.

Skulstad et al., "Grading of Myocardial Dysfunction by Tissue Doppler Echocardiography," Journal of the American College of Cardiology, vol. 47, No. 8, 2006, pp. 1672-1682.

Hoff et al., "Measurement of Heart Motion using Accelerometers," Proceedings of the 26th Annual International Conference of the IEEE EMBS, CA, USA, Sep. 1-5, 2004, pp. 2049-2051, XP-002467655.

Grimnes et al., "Velocity and Position Approximations from Left Ventricular 3D Accelerometer Data," Proceedings of the 30th Annual Northeast Bioengineering Conference, 2004, pp. 25-26.

* cited by examiner

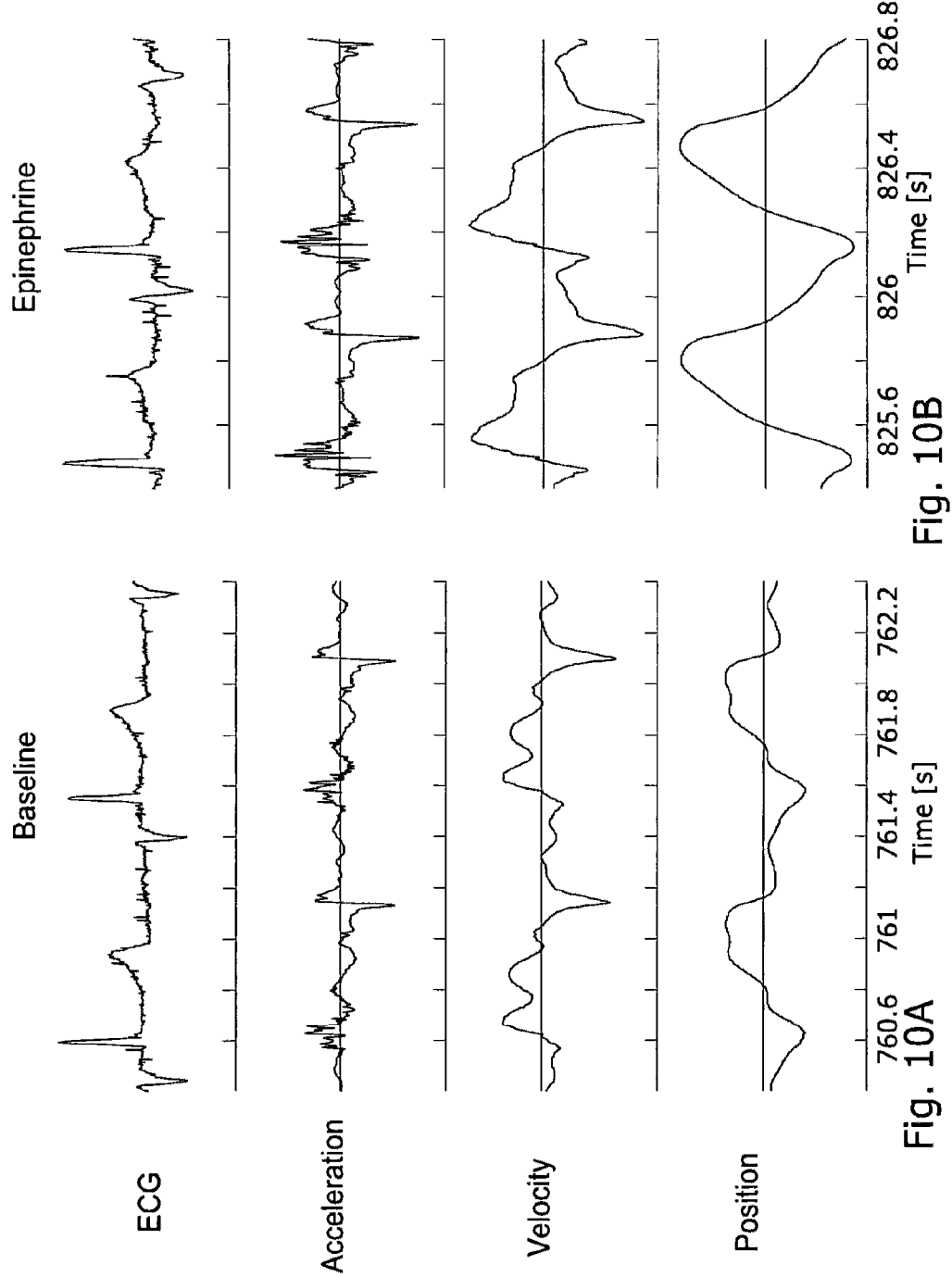

METHOD FOR ESTIMATING CARDIAC PUMPING CAPACITY

FIELD OF THE INVENTION

The present invention relates to estimating changes in cardiac pumping capacity in response to an intervention, in particular from data recorded by an accelerometer positioned on the heart.

BACKGROUND OF THE INVENTION

During and after cardiac surgery, it is of interest to monitor the performance of the heart, especially the responses to various forms of treatment.

One way to obtain data related to various aspects of the performance of the heart is by a motion sensor on or in the heart to measure the movement of the heart wall. A number of references describe the use of such motion sensors to obtain data related to specific performance parameters.

WO 03/061473 describes the use of an accelerometer fastened on a surface part of a heart to detect the movements of this surface part, e.g. in order to detect ischemia in this surface part.

U.S. Pat. No. 5,628,777 describes motion sensors integrated in large patches or electrodes having the function of delivering electrical stimulation signals, i.e. pacing the heart. The signals from the motion sensors are used to detect arrhythmia in order to trigger deliverance of the electrical stimulation signals.

U.S. Pat. No. 7,139,609 describes derivation of parameters representative of heart function, such as stroke volume, cardiac output, blood pressure, from acceleration signals representative of the acceleration of tissue within the patient.

In today's setup, a lot of data obtained from different individual apparatus are presented to the surgeon or cardiologist, who can thereby get a feeling for the global heart function and its response to an applied treatment. In order to simplify the equipment and provide a more objective estimate of the global heart function, an improved scenario for estimating changes in cardiac pumping capacity would be advantageous.

SUMMARY OF THE INVENTION

It may be seen as an object of the present invention to provide a method for estimating changes in cardiac pumping capacity as well as a system for analyzing data correlating with the pumping capacity of a heart, that solves the above mentioned problems of the prior art.

In the following description, it is shown that it is possible to directly correlate changes in cardiac pumping capacity to changes in parameters or graphical representation derived from signals characteristic to the acceleration of selected surface parts of the heart. In particular, it is shown how the effect of interventions, such as changes in intravascular volume or administration of medicaments, can be directly read from these parameters or graphical representations, and that these can thereby assist in decisions regarding the adjustment or administration of such.

Hence, with the overall goal of optimizing cardiac pumping capacity of cardiac surgery patients, it is another object of the invention to provide a tool, such as a system or a method, for assisting a decision relating to intravenous administration of medicaments to, or changes in the intravascular volume of, cardiac surgery patients.

In a first embodiment, the invention provides a system for assisting a decision relating to intravenous administration of medicaments to, or changes in the intravascular volume of, a cardiac surgery patient according to claim 1.

Throughout the specification and claims, LAD means left anterior descending artery, CX means circumflex artery, and RCA means right coronary artery.

In a second embodiment, the invention provides a method for assisting a decision relating to changes in the intravascular volume in a cardiac surgery patient according to claim 4.

In the second embodiment, the phrase change in intravascular volume preferably comprises adjustment of the fluid filling by intravenous loading fluid, i.e. increase filling and/or extracting fluid, i.e. decrease filling, since this is a common post-surgery intervention for cardiac surgery patients. In the following, the phrase administering fluid is also meant to encompass extracting fluid to decrease fluid filling. Also, changes in intravascular volume may comprise loss of liquid by other causes such as bleeding, sweating and diarrhea which can usually be halted to some degree or compensated (reversed) by appropriate fluid filling.

In a third embodiment, the invention provides a method for assisting a decision relating to intravenous administration of nitroprusside and/or betablocker and/or epinephrine to a cardiac surgery patient according to claim 10.

In a fourth embodiment, the invention provides use of an acceleration signal to assist a decision relating to intravenous administration of nitroprusside and/or betablocker and/or epinephrine to, or changes in the intravascular volume of, a cardiac surgery patient during post surgery monitoring according to claim 11.

In the following description, each preferred or optional feature or element may be combined or used by itself and applied to any of the above embodiments, where appropriate.

Throughout the description, the readout or initial analysis of the obtained acceleration signal may comprise:
  integration of the acceleration signal to obtain a velocity signal characteristic to relative velocities of said outer surface part as a function of time, and optionally
  double integration of the acceleration signal to obtain a position signal characteristic to relative displacements of said outer surface part as a function of time.

For the purpose of brevity and unless indicated otherwise, whenever reference to the "obtained signal" is made, this is to be interpreted as "the acceleration signal and/or integrated signals thereof representing relative velocities and/or displacements of the outer surface part as a function of time".

Preferably, the estimation of, or generation of results which correlates with, cardiac pumping capacity comprises providing signal interpretation data giving a correlation between the obtained signal, or signals derived there from, and cardiac pumping capacity. Such signal interpretation data is advantageous in that it eases the interpretation of the obtained signal, and enables even inexperienced operators to estimate cardiac pumping capacity. A simple example of signal interpretation data may be a table which in combination with an algorithm extracts a value from the obtained signal and correlates it with a cardiac pumping capacity scale, e.g. numbers from 1 to 10, with 1 being normal and 10 being fatal.

In alternative approaches, the obtained signals are obtained over a period of time, so that a change in the obtained signals may be determined. In such cases, the parameter and/or graphical representation of the first embodiment may correlate with a change in cardiac pumping capacity. Similarly, for the other embodiments, it is changes in cardiac pumping capacity which is estimated.

Preferably, the estimate, parameter or graphical representation, is generated over a period of time including or following changes in intravascular volume or intravenous administration of a medicament affecting the cardiac pumping capacity, and the method further comprises monitoring a change in the cardiac pumping capacity during this period of time. This is advantageous, as the operator is often interested in improving the cardiac pumping capacity, and need immediate response to whether a provided treatment succeeds in doing this.

Also, the system, method and use is configured or adapted to be used in automated long term monitoring such as post-surgery monitoring, where a skilled care-taker cannot be applying non-automated monitoring techniques.

In a preferred graphical representation, the acceleration signal comprises components along three different directions (hence, here the accelerometer is a triaxial accelerometer) and is presented as a parametric curve of the obtained signal in a three dimensional graph with axes corresponding to the three different directions. Examples of such representation may be seen in FIGS. 3-5. Such graphical representation allows the operator to get an intuitive feeling of the pumping capacity, and especially changes in pumping capacity over time. Various filtering of the signal are preferably conducted, as will be described in detail in relation to specific embodiments As can be seen from the examples, three dimensions are generally needed to describe the complete movement of the outer surface part, i.e. the movement of a point on this surface is not restricted to one dimension. Hence, presenting all three directions means that it is easy to see the direction in which the largest displacement occurs regardless of how the accelerometer is oriented.

Often, it is of interest to differentiate changes in cardiac pump capacity to different stages of the cardiac cycle. For this purpose, it may be preferred to also obtain an electrocardiogram and/or blood pressures from the subject while obtaining the acceleration signal, and co-register or correlate the obtained signal with electrocardiogram and/or blood pressures to obtain the acceleration, velocity and/or position during different stages of the cardiac cycle, e.g. in the form of a parametric curve in a two- or three dimensional graph. This feature enables extraction of parameters or graphical representations related to specific stages of the cardiac cycle, which may be particularly advantageous when monitoring the effect of treatments known to affect individual stages. Thus, it may be preferred to calculate and/or display the length of a segment of the curve corresponding to one or more stages of the cardiac cycle. Such length, or a number derived there from, may form a parameter correlating with cardiac pumping capacity in accordance with the various embodiments of the invention. Also, the area of a region circumscribed by the parametric curve during a cardiac cycle may be determined and presented as the generated parameter or graphical representation.

In a preferred embodiment, the blood pressure correlated with the obtained signals is periphery blood pressure. This provides the advantage of being simple, non-invasive measurement.

As there is no absolute measure for cardiac pumping capacity, the various embodiments relates to determining or monitoring changes in cardiac pumping capacity, or generating relative parameters or estimates of cardiac pumping capacity. A number of treatments have a very direct effect on the cardiac pumping capacity, typically related to specific stages of the cardiac cycle. Examples may be administration of fluid or drugs such as betablocker or epinephrine (adrenaline). In order to determine the effect of such treatment, it is advantageous for the operator to use embodiments of the present invention to follow the development of cardiac pumping capacity in a subject over time.

The system according to the first embodiment allows the user to store the generated parameter or graphical representation corresponding to the cardiac pumping capacity at a given time (a baseline), and presenting it in relation to parameters or graphical representations generated at later times to enable estimating a change in the cardiac pumping capacity over time. This function is intended to be activated by the cardiologist several times both during medical intervention and in post surgery monitoring in order to follow the progress of the subject.

In the alternative, a baseline which corresponds to normal cardiac pumping capacity, which may not originate from the subject, may be presented together with the corresponding estimate, parameter or graphical representation generated from the signal obtained from the subject. This would provide an aim for the operator and at the same time provide an indication of the degree of insufficiency in the present cardiac pumping capacity.

When the effect of an intervention is known, the operator can use this knowledge as an assistance when deciding whether to continue, halt (, or reverse) the intervention. Thus, the methods may further comprise forming a decision relating to an intravenous administration of a fluid or a medicament affecting the cardiac pumping capacity based on the provided estimate.

It is preferred that the accelerometer measures acceleration components in two or more different directions, preferably three, so that the acceleration signal may obtain components corresponding to these different directions. In an initial data analysis, modulus signal, a projection or the largest component may be extracted for further processing.

Further, a second accelerometer to be positioned on, in or just below a second outer surface part of the myocardium may be used to generate a second acceleration signal which may be used in the same way as the (first) acceleration signal.

The basic idea of the invention is to obtain and analyze data characteristic to accelerations of an outer surface part of a myocardium to generate parametric curves as a function of time, which allows an operator to monitor a change in cardiac pumping capacity resulting from intravenous administration of medicaments or changes in intravascular volume.

That such acceleration data largely correlates to cardiac pumping capacity is not obvious as the cardiac pumping capacity is in itself a very complex concept. Cardiac pumping capacity may be quantified by the cardiac output (CO) which may be set up as the product of heart rate (HR) and stroke volume (SV):

$$CO = HR \times SV$$

For a 70 kg man normal values are HR=70/min and SV=70 mL, giving a cardiac output of about 5 L/min.

Briefly described, stroke volume is mainly determined by three main factors: preload, afterload and contractility. Preload is the ventricular volume at the end of diastole, and an increased preload leads to an increased stroke volume. Preload is mainly dependent on the return of venous blood from the body. Venous return is influenced by changes in position, intra-thoracic pressure, blood volume and the balance of constriction and dilatation (tone) in the venous system. Afterload is the resistance to ventricular ejection. This is caused by the resistance to flow in the systemic circulation and is the systemic vascular resistance, determined mainly by the diameter of the arterioles and pre-capillary sphincters. Contractility describes the ability of the myocardium to contract in the absence of any changes in preload or afterload. The most important influence on contractility is the sympathetic nervous system.

Thus, cardiac pumping capacity is a complicated function of a large number of parameters, it is typically quantified through the cardiac output by the heart rate and the stroke volume, but the algebraic approaches are only approximate and do typically not represent the full picture. It is therefore difficult to calculate CO based on measurement of the variables on which it depends, and is therefore typically measured by Tissue Doppler echocardiography, which is however not suitable for long term monitoring such as post-surgery monitoring.

Thus, the invention provides the advantage of presenting complex data in a simple way, so that subtle effects of administering medicaments or changes in intravascular volume can be monitored and reacted upon.

These and other embodiments of the invention will be apparent from the following description with reference to the described embodiments.

BRIEF DESCRIPTION OF THE FIGURES

The various embodiments of the invention will now be described in more detail with regard to the accompanying figures. The figures are not to be construed as being limiting to other possible embodiments falling within the scope of the attached claim set.

FIGS. 7-11 show acceleration, velocity and position signals correlated with ECG signals for a number of different treatments.

DETAILED DESCRIPTION OF THE INVENTION

Figure 1:
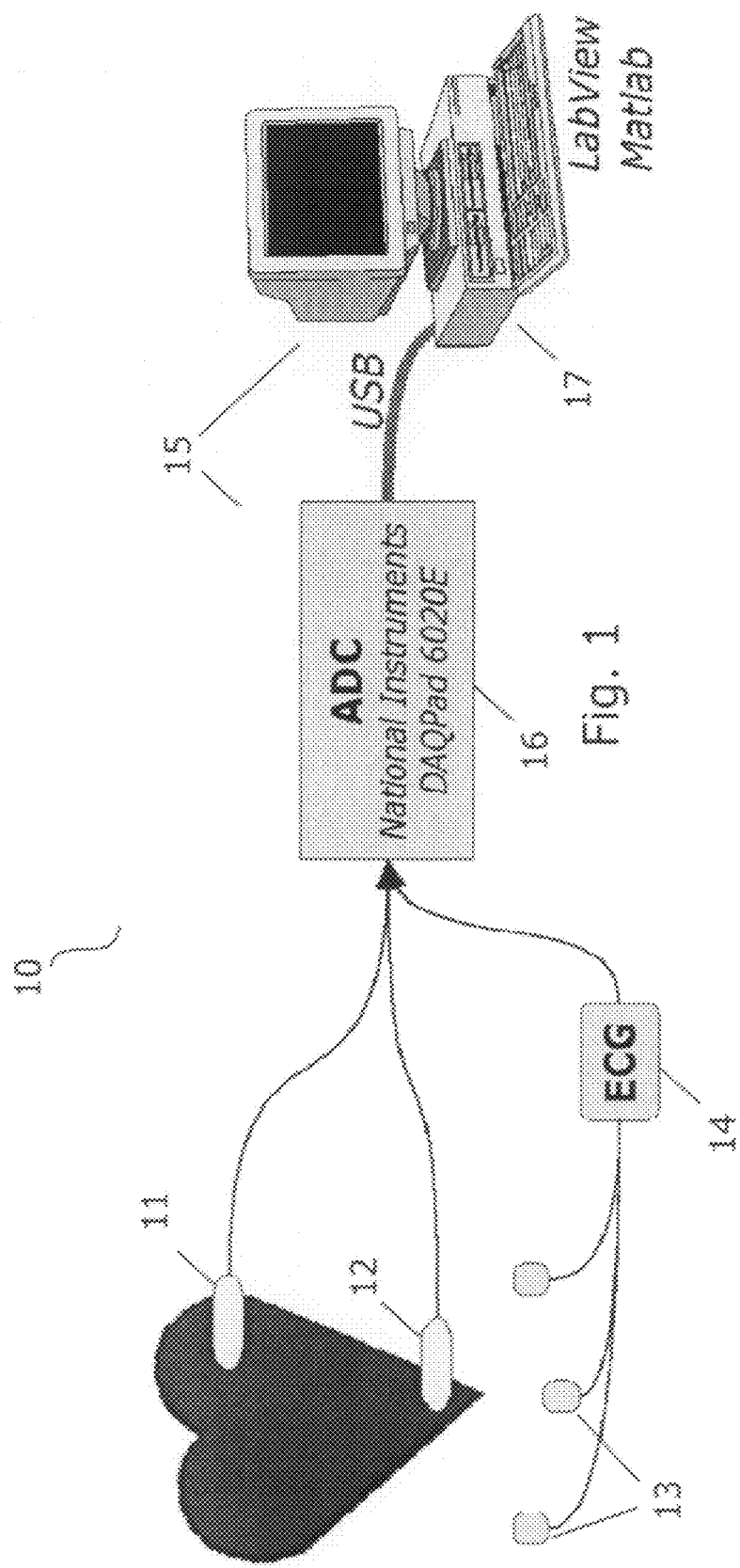
FIG. 1 illustrates a system for estimating changes in cardiac pumping capacity according to an embodiment of the invention.

A system 10 for estimating changes in cardiac pumping capacity in response to an intervention according to an embodiment of the invention is illustrated in FIG. 1. The system comprises a first accelerometer sensor 11 to be positioned on the heart, and being connected to an external signal processing device 15 for receiving and processing the acceleration signal as will be described in greater detail later. The signal processing device 15 in this case comprises a device 16 for pre-processing data, typically AD conversion and initial filtering, as well as a computer 17 running software means for data acquisition, processing, presentation, and user interfacing. In this example, the pre-processing device is an ADC from National Instruments.

In addition to the first accelerometer sensor 11, data can be collected from a second accelerometer sensor 12 positioned elsewhere on the heart. Also, subject ECG is typically monitored by ECG electrodes 13 and ECG apparatus 14. The ECG data may be collected and co-registered with the obtained signal to divide it into segments corresponding to stages of the heart cycle.

Figure 2B:
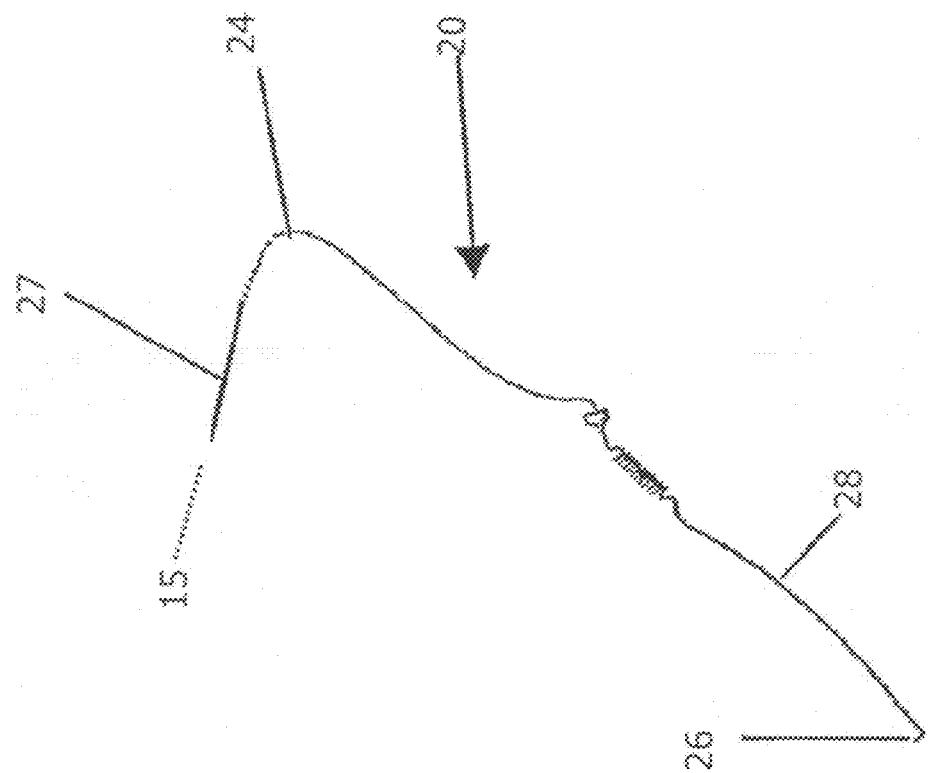
FIGS. 2A and B examples where the accelerometer is fitted on a commercially available temporary pacemaker electrode.
Figure 2A:
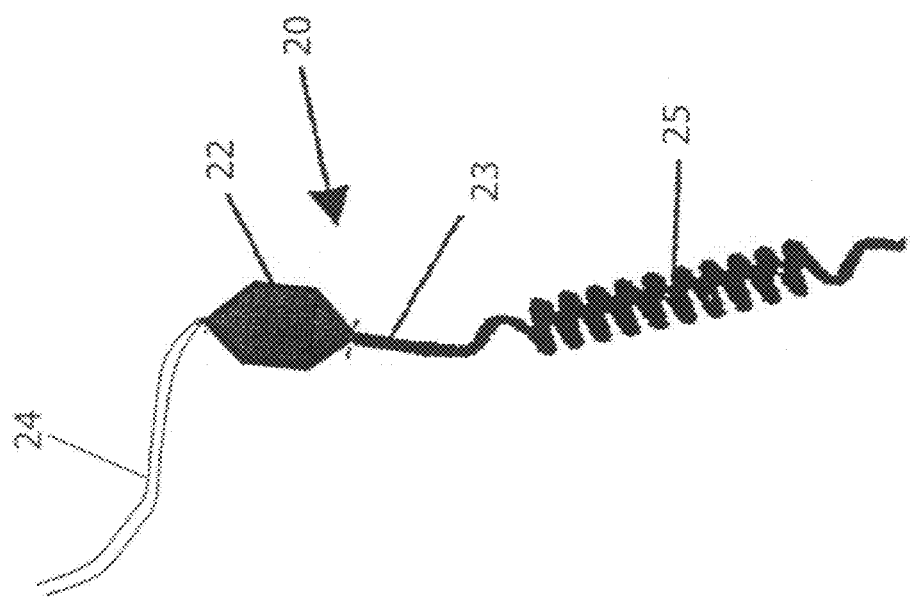

FIGS. 2A and B illustrate a setup 20 illustrating a specific example of the accelerometer sensor 11 from FIG. 1, where an accelerometer 22 is fitted on a commonly known temporary pacemaker electrode.

Reference number 22 denotes the accelerometer arranged immediately above the conductive pacemaker electrode 23. The accelerometer sensor 22 furthermore has a shape, indicated in FIG. 1A, which gives good contact with the heart muscle and at the same time allows it to be withdrawn from the heart muscle without damaging tissue etc. The 1-3-axis accelerometer 22 can be developed with micro-electro-mechanical or possibly nano-electro-mechanical methods (MEMS/NEMS) in order to make it small enough for being removed without the need for surgical intervention, and for being light and small enough to not hinder or disturb the movement of the heart and thereby enable an acceleration signal being characteristic to accelerations of an outer surface part of the myocardium.

At the end of wire section 28 is a hook shaped needle 26 for placing the electrode in the myocardium. The wire 25 has been given the form of a spring, and upon insertion, this is tightened to provide good contact between the accelerometer sensor 22 and the myocardium. Following insertion, the hook shaped needle 26 is cut, so that upon subsequent removal, the wire can be pulled out of the thorax area together with the accelerometer sensor without the need for surgical intervention, e.g. in a minimally invasive procedure.

Reference number 24 denotes insulated conductors providing means for transmitting the obtained acceleration signal from the accelerometer. The conductors 24 can be connected to an external signal processing device 15 as illustrated in FIG. 1. At the end of the wire 24 is provided with a straight needle 27 to allow the wire to be passed through the patient's thorax to the pacemaker machine.

The construction of the setup 20 is not dependent on the sensor also being equipped with a temporary pacemaker electrode.

In the following, a number of different ways to analyze obtained signals and present them in a way enabling an operator to monitor a change in cardiac pumping capacity will be presented. The embodiments illustrate the ability to monitor the change in cardiac pumping capacity related to administration of medicaments or changes in intravascular volume.

For all embodiments, the obtained signal comprises three acceleration components in three orthogonal directions recorded by a tri-axial accelerometer positioned on an outer surface part of the myocardium of the heart and being characteristic to accelerations of this outer surface part as a function of time. Results from two accelerometer positions are used, a first positioned in the region of the supply area of the LAD coronary artery and a second one positioned in the supply area of the Circumflex coronary artery. The accelerometers where fastened by suture with two sutures. Both accelerometers were Kionix KXM52-1050(xyz), from Kionix Inc. Itaca, USA.

Simultaneous monitoring of CO by traditional direct measurement of blood flow (requires surgical intervention) ensures data for that can be used for correlating the accelerometer data, or parameters derived there from, with CO.

The raw accelerometer data were filtered by an analogue low-pass filter (LP-filter) according to specifications from the sensor supplier. A filter giving a bandwidth of about 100 Hz was chosen for noise reduction. This will also work as an antialiasing filter. The continuous low-pass filtered acceleration signal is AD-converted, and thereafter high-pass filtered (HP-filter) at 1 Hz to remove/reduce gravity and respiration components. The signal was integrated once to get the velocity signal and a second time to get the position or displacement signal. The signals were HP-filtered after each integration to reduce respiration components further. Labview (National Instruments Inc., Austin, Tex., USA) was used for data acquisition. MatLab (The MathWorks, Inc., Natick, Mass., USA) was used for signal processing and visualization.

Figure 3:
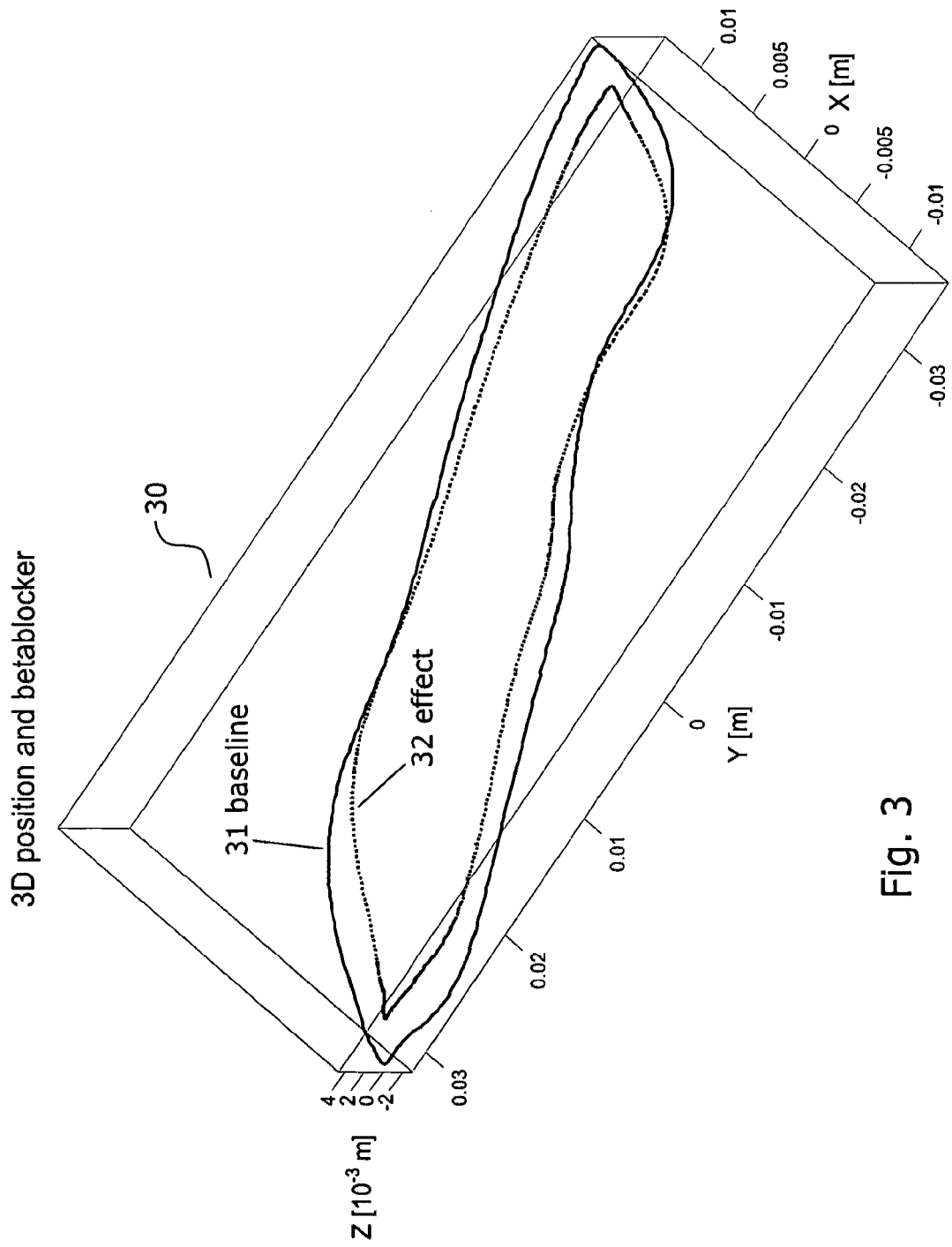
FIGS. 3-6 show parametric 3D position curves for a number of different treatments.

FIG. 3 shows parametric 3D-position curves for the outer surface part of the heart wall during one heart beat. The curves are shown in a three dimensional graph 30 with axes corresponding to the three different directions. Similar parametric curves can be made in a graph having accelerations or velocities in the three directions on the axes instead. Curves corresponding to a first time before administration of betablocker (baseline 31) and a second, later time (effect 32) are shown allowing monitoring a change in cardiac pumping capacity over a period of time including the administration.

Betablocker has the effect of reducing the contraction stage of the heart. The effect of the betablocker is manifested in a markedly decrease in the length, i.e. displacement amplitude in the direction of largest amplitude, of the 3D-position curve, i.e. the movement of the heart wall was reduced. Simultaneous monitoring of cardiac output showed a reduction from 3.6 L/min to 3.0 L/min over the same period. Thus, the visual appearance of the parametric curve can form a graphical representation for monitoring changes in cardiac pumping capacity in accordance with the various embodiments of the invention. The length of the 3D-position entire parametric curve (circumference), or from selected segments of it (please refer to FIGS. 5 and 6), can thereby form a parameter for monitoring changes in cardiac pumping capacity related to administration of betablocker in accordance with the various embodiments of the invention. The monitored changes can be used by the cardiologist, or other trained personnel, to assist a decision of whether to continue or halt the administration of betablocker.

As can be seen from FIG. 3, the change in position, i.e. displacement, is symmetric for the three axes so that the parametric curve is not distorted. The same applies to the corresponding parametric curves for acceleration and velocity (not shown). With this 3D-position method the pumping capacity of the heart can be monitored, also without the use of any additional data, such as EGG or pressures. Thus, shape and/or circumference length of the 3D-position curve, or a number derived therefrom, may form a parameter or a graphical representation for monitoring changes in cardiac pumping capacity in accordance with the various embodiments of the invention.

As will be illustrated in relation to FIGS. 5 and 6 later, the parametric curves can be correlated with the different stages of the cardiac cycle. For administration of betablocker, such correlation of corresponding curves for acceleration and velocity reveals that the reduction in amplitude resulting from betablocker was primarily due to a lower acceleration and velocity in the systolic stage. This means that an operator can, by comparing a parametric curve for a given heart with corresponding curve for a heart with normal cardiac pumping capacity, determine the change or difference and relate it to a treatment for improving cardiac pumping capacity, provide the treatment, and follow that the provided treatment has the desired effect on the cardiac pumping capacity.

Figure 4:
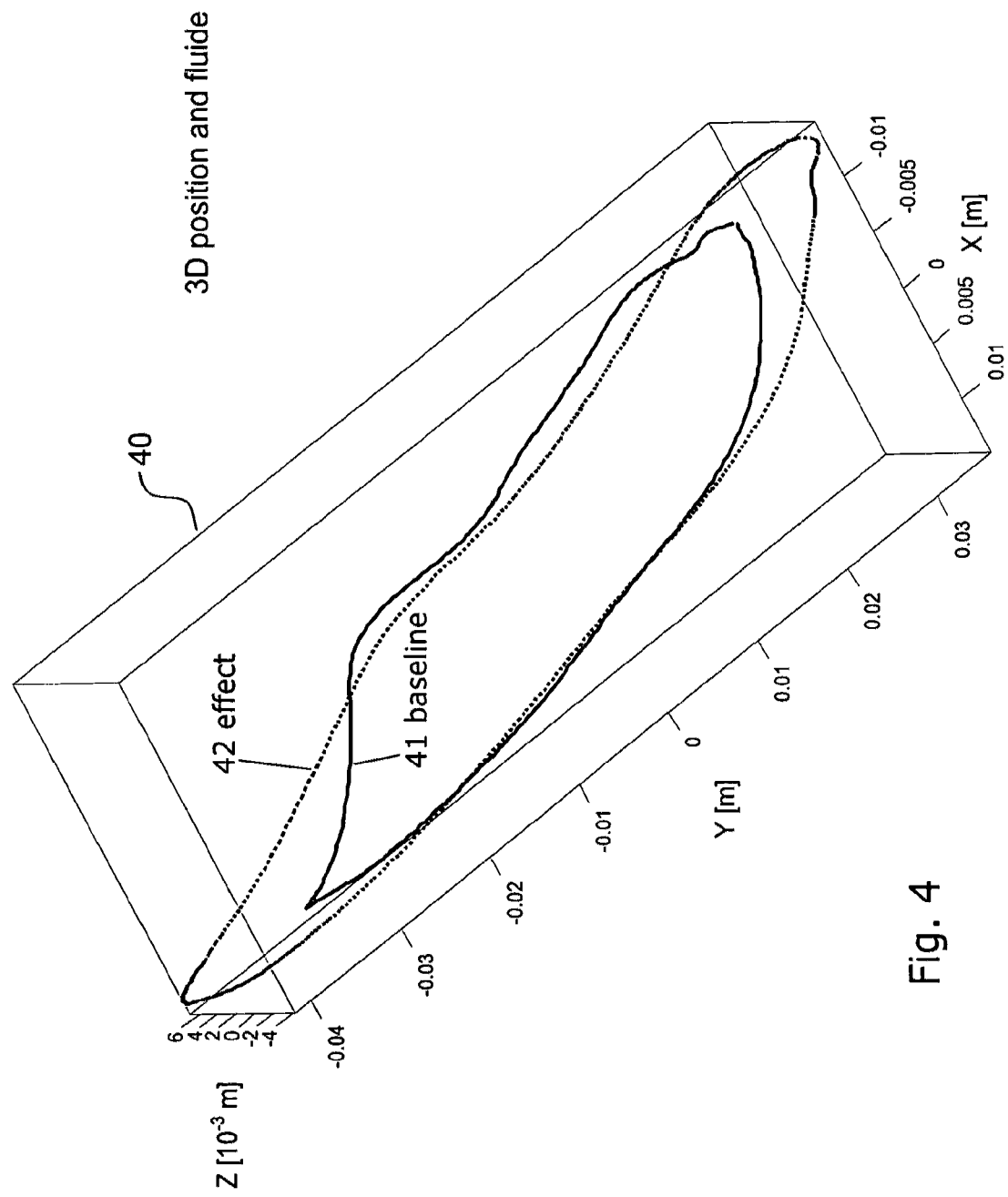

FIG. 4 is a graph 40 showing the 3D-position curves describe the heart wall motion during one heart beat before (baseline 41) and after (effect 42) fluid loading, i.e. an example of a change in intravascular volume. As fluid can both be added and removed, the order of the curves can be reversed to see the effect of reducing the fluid filling. The length of the 3D-position curve is clearly increased by fluid loading, i.e. the movement of the heart was enlarged. A simultaneous raise in cardiac output from 3.8 L min-1 to 4.7 L min-1 was observed.

Increasing fluid results in increased filling of the heart, and will decrease systolic acceleration and velocity amplitudes, but increase the displacement amplitude. Reducing fluid results in reduced filling of the heart, and will increase the acceleration and velocity amplitudes, but decreases displacement amplitude.

This is because for the reduced filling and reduced afterload (nitroprusside effect), the systolic contraction is characterized by a high but very short peak acceleration and velocity. This is due to the heart being emptier and there is less blood inside the heart to be ejected during the systole. In addition the afterload is decreased meaning that the resistance for ejection of the blood is lower.

Increased filling has a somewhat opposite effect: Increased filling of the heart means that blood volume inside the heart is higher. Thus, by the Starling mechanism the heart should contract more—and it does. But because of the increased volume, it takes longer time to eject the blood during the systole. Thus, despite an increased contraction for increased filling, we observe a lower acceleration and velocity amplitudes in 3D parametric curves corresponding to that of FIG. 4, but with accelerations or velocities along axes.

Again, this means that an operator can compare the parametric curves with curves for normal or previous cardiac pumping capacity, determine the nature of the change and relate it to a treatment for improving cardiac pumping capacity, provide the treatment, and follow that the provided treatment has the desired effect on the cardiac pumping capacity, i.e. bringing the parametric curve back to normal performance, such as to the baseline.

Hence, the visual appearance of the parametric curve (acceleration, velocity or position) can form a graphical representation for monitoring changes in cardiac pumping capacity in accordance with the various embodiments of the invention. Similarly, the length of the entire parametric curve (circumference for one cardiac cycle), or from selected segments of it (please refer to FIGS. 5 and 6), can thereby form a parameter for monitoring changes in cardiac pumping capacity related to adjustment of fluid filling in accordance with the various embodiments of the invention. The monitored changes can be used by the cardiologist, or other trained personnel, to assist a decision of whether to continue, halt or reverse the fluid filling adjustment.

For the above mentioned reasons, administrating nitroprusside (reduced filling and afterload) tend to decrease the displacement amplitude and giving fluid (increased filling) tends to increase the displacement amplitude. The monitored changes can thus also be used by the cardiologist, or other trained personnel, to assist a decision of whether to continue or halt administration of nitroprusside, and whether it has had the desired effect.

Figure 5:
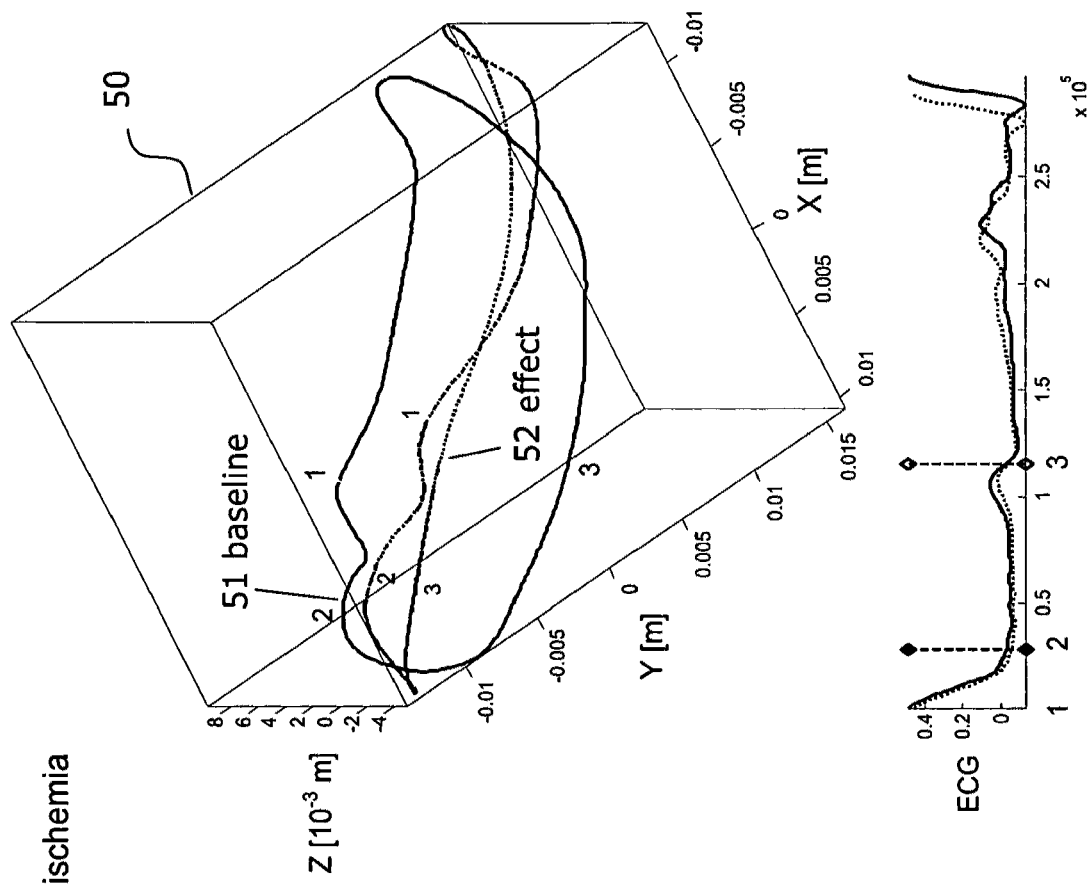

FIG. 5 is a graph 50 showing 3D-position curves describe the heart wall motion during one heart beat before (baseline 51) and after (effect 52) occlusion of the LAD (Left Anterior Descending) to create ischemia. Both myocardial ischemia and betablockers (FIG. 3) reduces the pumping capacity of the heart, but the 3D-position curves are very different since myocardial ischemia induces an abnormal movement of the heart wall. Twisting of the 3D-curve appeared during myocardial ischemia while the shape of curve did not change when a betablocker was given (FIG. 3).

Figure 6:
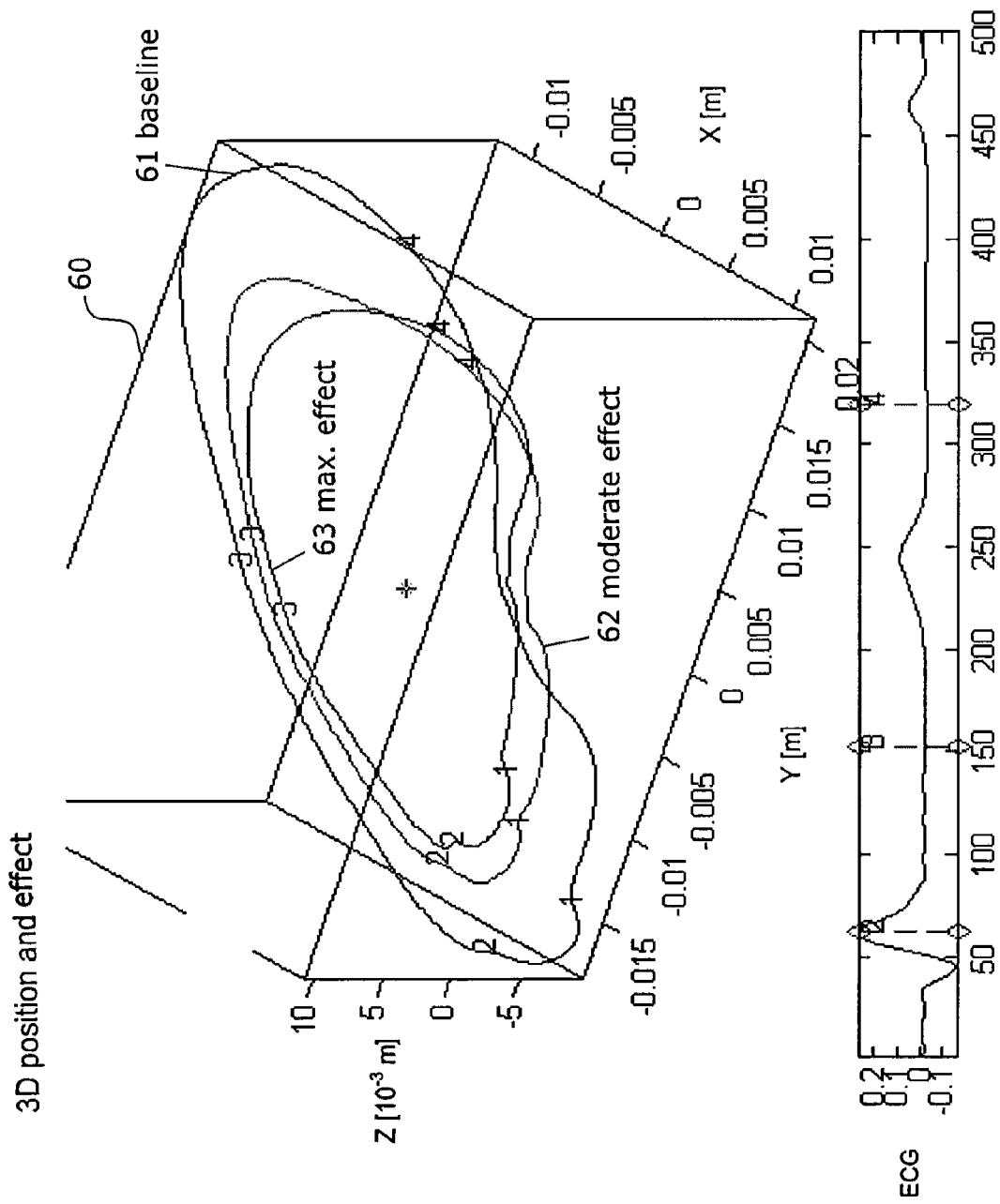

FIG. 6 is a graph 60 showing 3D-position curves describe the heart wall motion during one heart beat before (baseline 61), after moderate effect (62), and after maximum effect (63) during intravenous administration of nitroprusside and/or betablocker and/or epinephrine or a change in intravascular volume.

As illustrated in FIGS. 5 and 6, a simultaneously recorded ECG is correlated to the obtained signal, and segments of the parametric curve are assigned to stages of the cardiac cycle (reference numbers 1-4). In both FIGS. 5 and 6, significant changes in both circumference and length in different segments before and after intervention can be seen directly. By standard mathematical plotting programs, the precise length of one or more segments of the parametric curve, or the circumference of the entire curve, can be determined, and the development of such parameter can be followed during the intervention.

FIGS. 3-6 show that 3D-accelerometer sensor data can be sufficient to monitor the changes in pumping capacity of the heart caused by administration of medicaments or changes in intravascular volume. Additional information can be achieved by combining ECG and/or pressure with the accelerometer signal so that the systole and diastole can be defined as will be shown in the following. This gives a more precise description of the cardiac pumping capacity.

FIGS. 7 through 11 presents accelerations, and/or velocities and/or positions correlated to simultaneously recorded ECG or pressure signals. These data may be used to generate a multiplicity of parametric curves as a function of time in graphs having axes different combinations of signals, of which those shown in FIGS. 3-6, 12 and 13 are just examples. For the instances where only one acceleration, velocity or position signal is used (e.g. FIGS. 8, 10 and 11), this may be either the signal from just one of the directions (e.g. the one with largest amplitudes), or the length of a sum-vector of signals from two or three of the directions such as $(a_x^2+a_y^2+a_z^2)^{1/2}$. For all such parametric curves, the total length (for one cardiac cycle) or lengths for segments can be determined and used as parameters or graphical representations for monitoring the effect of the associated intervention.

Figure 7:
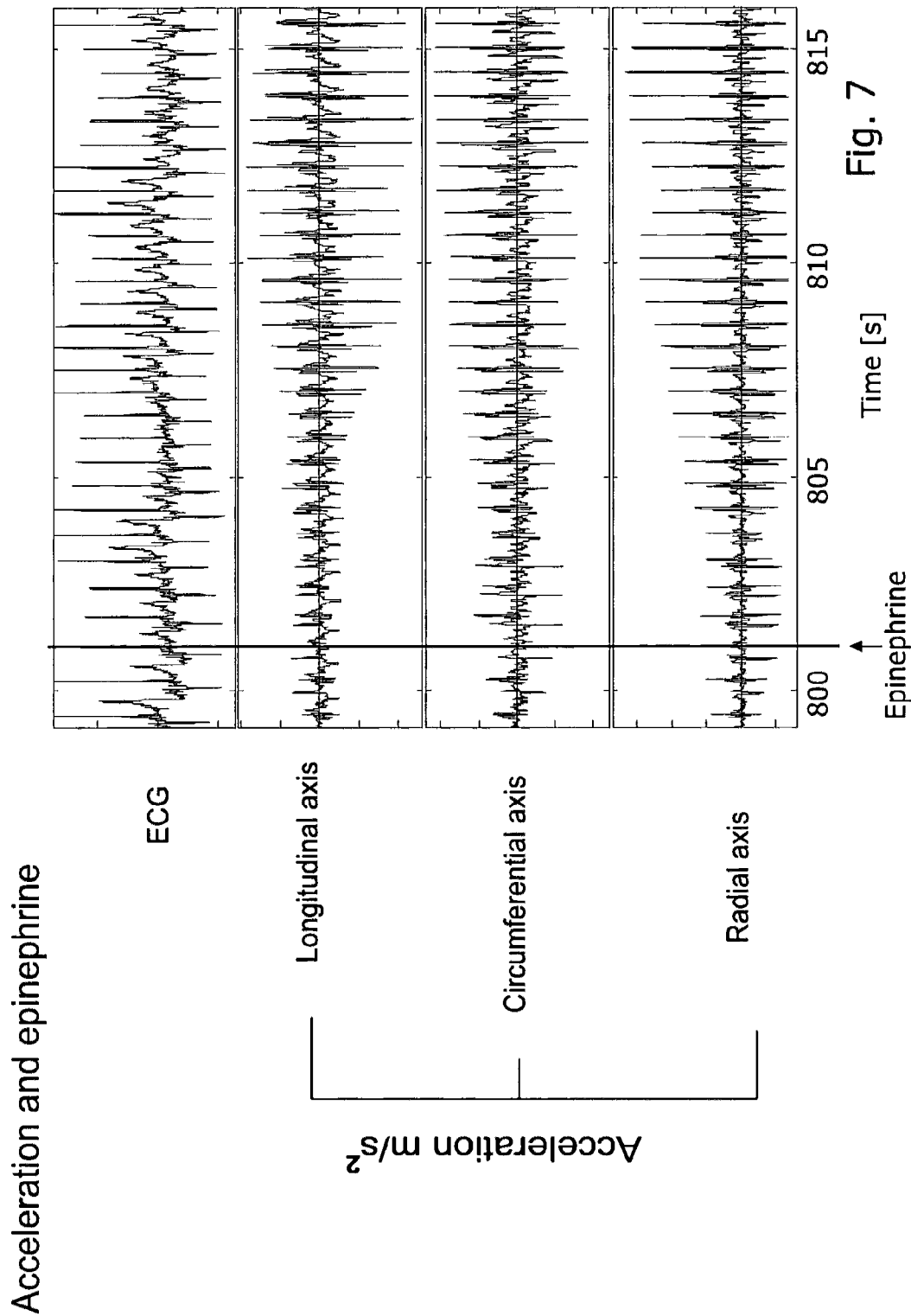

In FIG. 7, ECG and acceleration signals are recorded simultaneously and correlated, just before and after administration of epinephrine. The QRS on the ECG corresponds to peak systolic acceleration. As seen, the peak systolic acceleration is markedly increased in all axis during an infusion of epinephrine.

Figure 8:
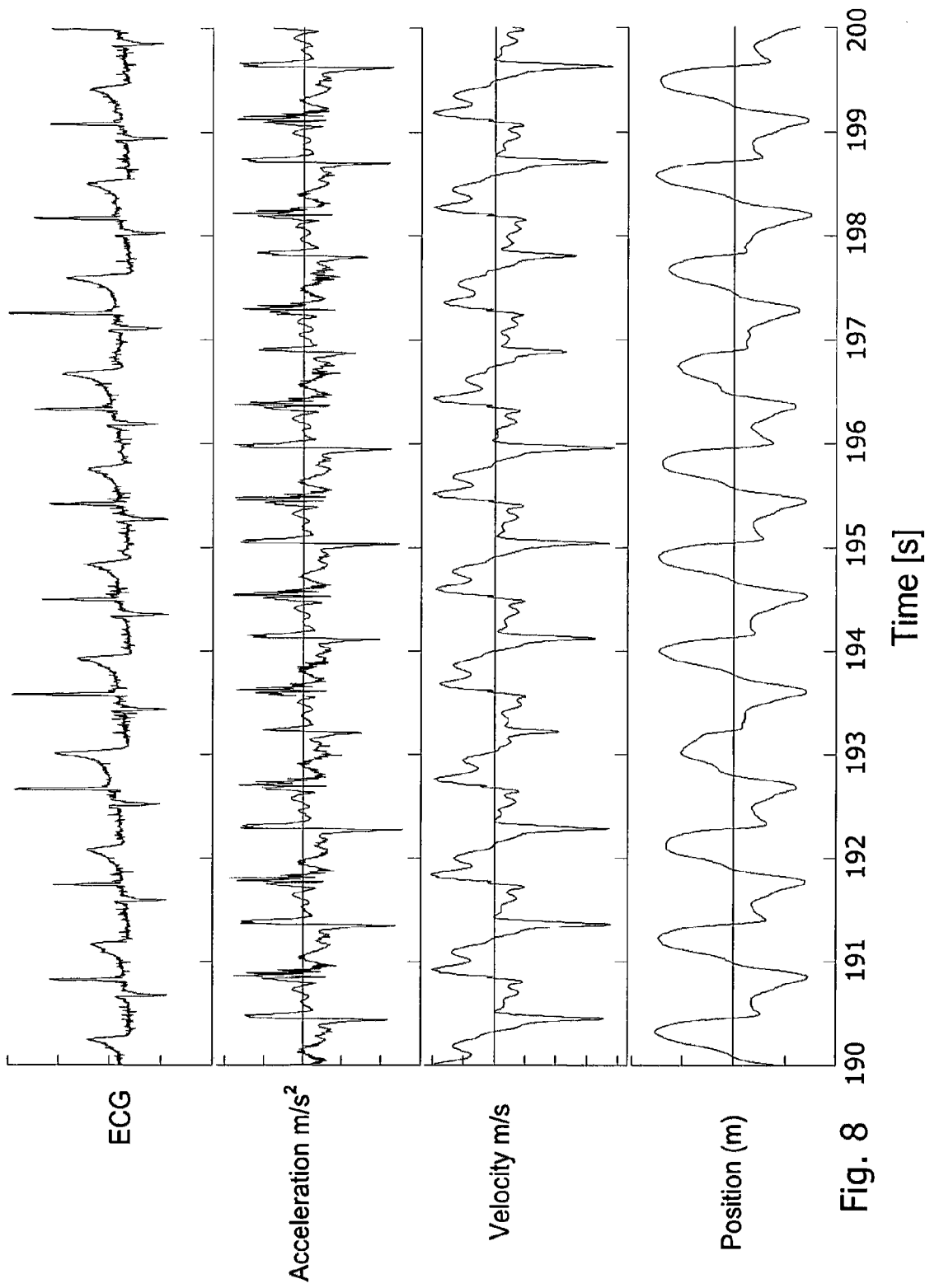

The accelerometer signals can be integrated once to velocity and twice to position. The interpretation of the acceleration curve can be difficult, for example one can have zero or small acceleration even though the velocity is high and visa versa. In addition, velocity and position are more accessible since these curves looks similar to tissue velocity, strain or displacement curves obtained by tissue Doppler echocardiography. Tissue Doppler echocardiography (TDE) is considered the clinical gold standard method for measuring the pumping capacity of the heart, but only intermittent readings are available with the this technique. In contrast, continuous monitoring over hours or even days is possible with the 3D-accelerometer, thereby making the technique suitable for post surgery monitoring. Since velocity, strain and displacement are well known TDE parameters, the integrated acceleration signals might be easier to interpret in a clinical setting. FIG. 8 shows an example of such continuous monitoring and the correlation between the various types of signals.

Figures 9A, 9B:
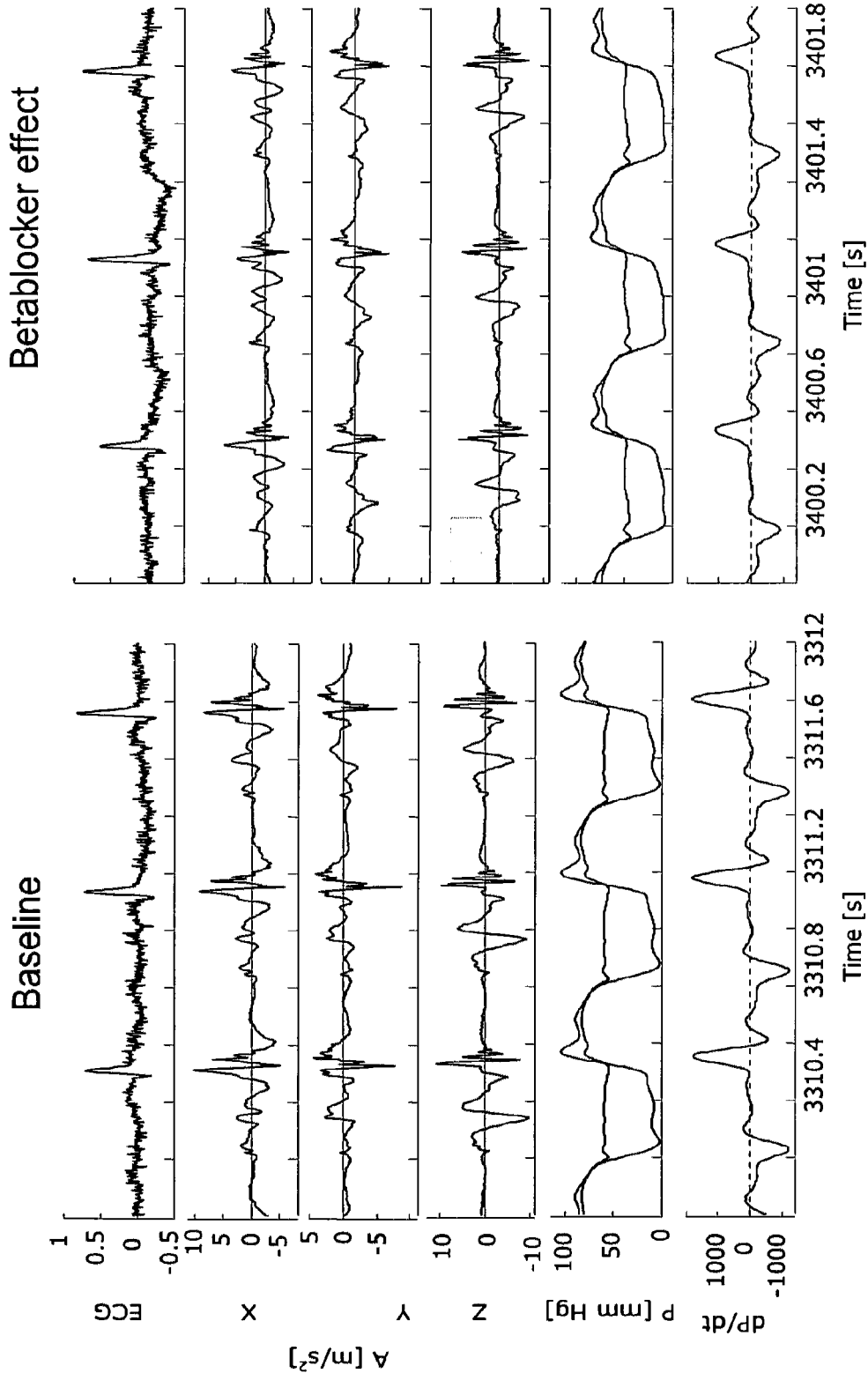

In FIGS. 9A and B, ECG, acceleration in three directions, left ventricle pressure and it's time derivate dP/dt, in addition to aortic pressure can be seen over a period of time before (9A) and after (9B) administration of betablocker.

In all axes a reduction in peak systolic acceleration can be seen during betablocker infusion.

In FIGS. 10A and B, ECG, acceleration, velocity and position are shown for periods before (10A) and after (10B) administration of epinephrine. An increase in peak acceleration, velocity and position was seen during epinephrine infusion. The changes correlated with cardiac output, indicating that peak systolic acceleration, velocity and position reflect the cardiac pumping capacity.

Figures 11A, 11B:
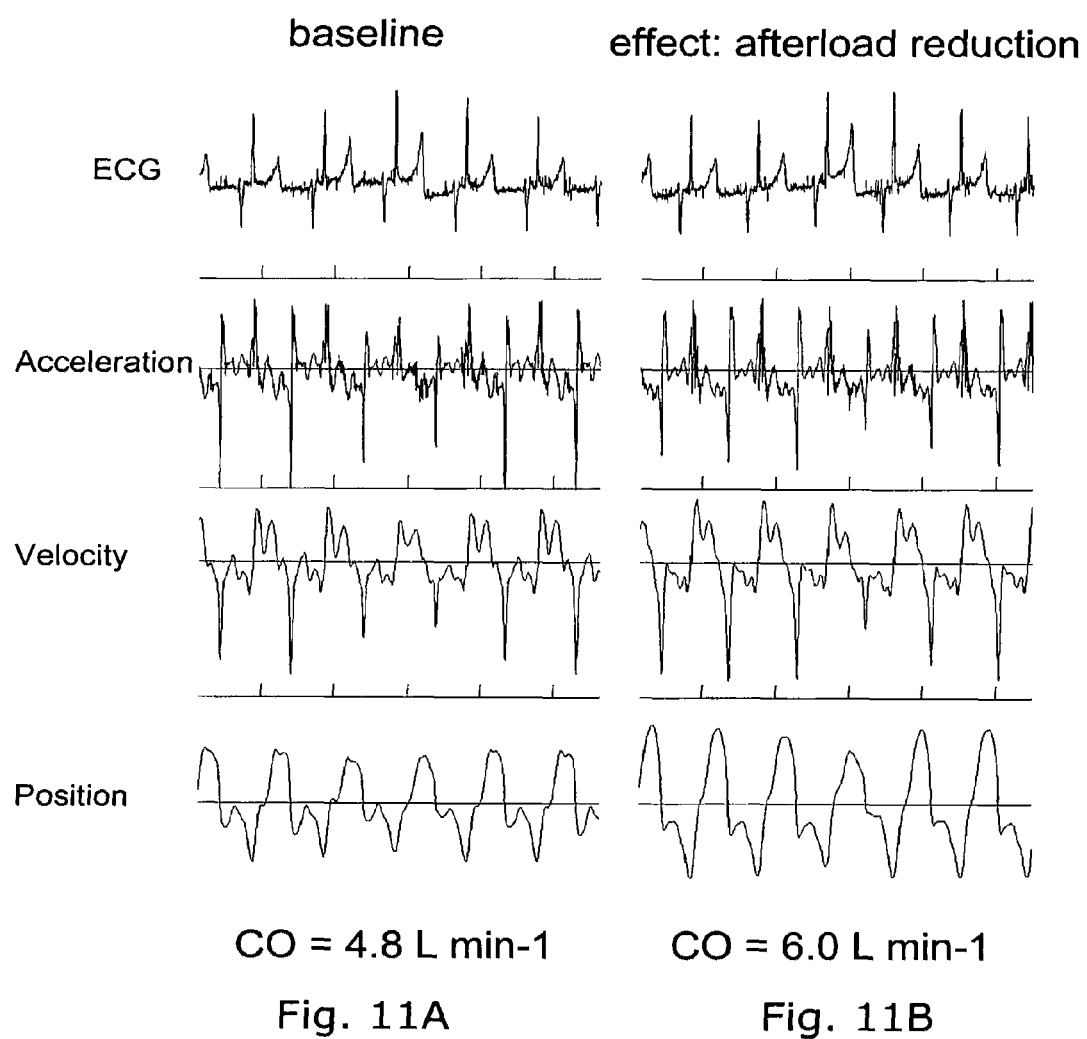

Even though systolic peak acceleration, velocity and position seem to reflect the pumping capacity of the heart during epinephrine and betablocker infusion, differences can be seen during afterload reduction by infusion of nitroprusside. In FIGS. 11A and B, ECG, acceleration, velocity and position are shown for periods before (11A) and during (11B) afterload reduction. Almost no change in the peak acceleration can be seen. In contrast, a marked increase in the displacement amplitude is present, implying an enlarged movement of the heart wall. The cardiac output simultaneously increased and therefore the amplitude of the position curve seems to reflect the pumping capacity of the heart most precisely.

Figure 12:
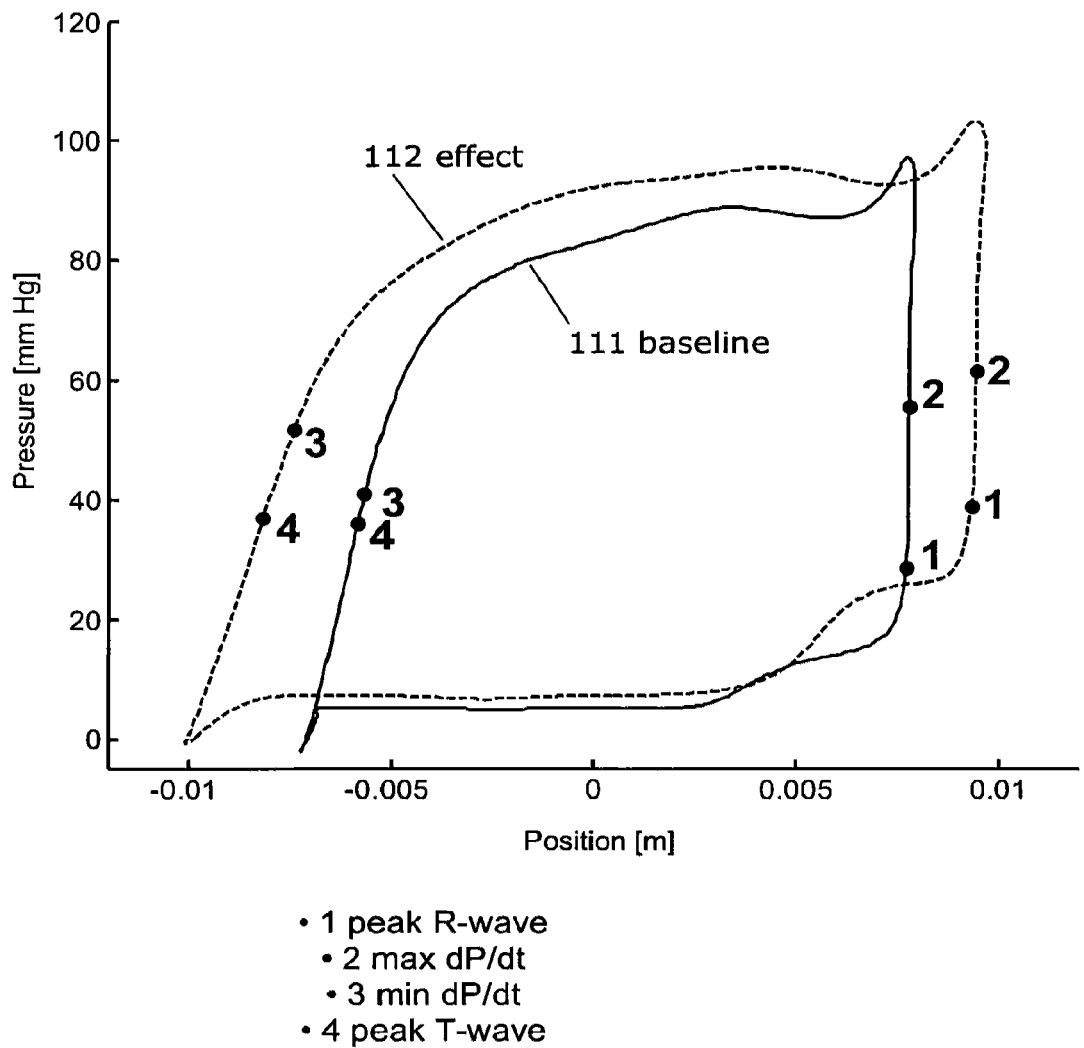
FIGS. 12 and 13 show pressure-position relationship for a number of different treatments.

FIG. 12 shows the relation between left ventricle pressure and the change in position (displacement) of the outer surface part for one heart cycle before (baseline 111) and after (effect 112) fluid loading. This parametric curve can be generated using some of the data from FIG. 8, and describes the pumping capacity of the heart since the area of the loops reflects cardiac work. As can be seen, fluid loading induces increased cardiac work as to be expected. The different numbers indicate different systolic and diastolic stages during one heart cycle. Hence, the visual appearance of the parametric curve can be used as a graphical representation for monitoring changes in cardiac pumping capacity in accordance with the various embodiments of the invention. Also, the area encircled by the curve can be calculated and be used as a parameter for monitoring changes in cardiac pumping capacity related to adjustment of fluid filling in accordance with the various embodiments of the invention.

As for FIGS. 5 and 6, simultaneously recorded blood pressure is correlated to the obtained signal, and segments of the parametric curve are assigned to stages of the cardiac cycle (reference numbers 1-4). By standard mathematical plotting programs, the length of one or more segments of the parametric curve, or the circumference of the entire curve, can be determined, and the development of such parameter can be followed during the intervention.

These monitored changes can be used by the cardiologist, or other trained personnel, to assist a decision of whether to continue, halt or reverse the fluid filling adjustment.

Figure 13:
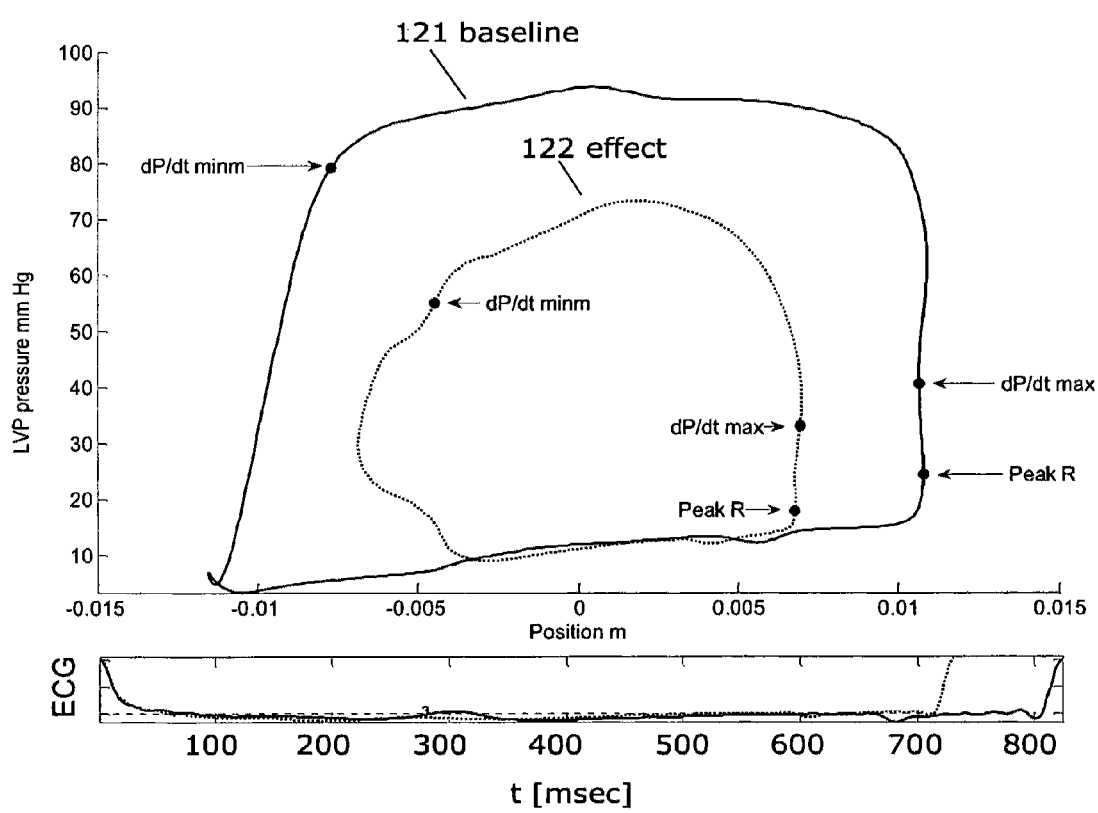

Similarly to FIG. 12, FIG. 13 shows the relationship between left ventricle pressure and position of the outer surface part before (baseline 121) and after (effect 122) administration of Betablocker. As seen, when administrating an intravenous betablocker, the area encircled by the curve (cardiac work) is markedly reduced.

As mentioned previously, Cardiac pumping capacity may be quantified by the cardiac output (CO) which may be set up as the product of heart rate (HR) and stroke volume (SV) by the relation: CO=HR×SV. To further demonstrate the correlation between the acceleration, velocity and position signals and cardiac pumping capacity, the following Tables 1-4 presents correlations between changes in CO, SV and HR (all related to the pumping capacity) and parameters extracted from the obtained signals.

Table 1 below shows the relationship between cardiac output as measured by state of the art methods and systolic displacement (i.e. the amplitude in the position signal) as determined by an embodiment of the present invention during different medical interventions.

TABLE 1

|  | Intervention | N | baseline | SE of mean | max effect | SE of mean | % change | T-test P-value |
|---|---|---|---|---|---|---|---|---|
| Cardiac output (L min −1) | Nitroprusside | 10 | 4.41 | (0.63) | 4.45 | (0.78) | 1% | 0.876 |
|  | Ephineprine | 10 | 4.27 | (0.54) | 6.80 | (0.93) | 59% | <0.001 |
|  | Betablocker | 10 | 4.53 | (0.68) | 3.89 | (0.66) | −14% | <0.001 |
|  | Fluid infusion | 11 | 4.05 | (0.45) | 4.96 | (0.49) | 22% | <0.001 |
| Systolic Displacement (millimeters) | Nitroprusside | 10 | 37.8 | (7.33) | 31.8 | (7.85) | −16% | 0.201 |
|  | Ephineprine | 10 | 38.8 | (6.85) | 55.9 | (9.1) | 44% | <0.001 |
|  | Betablocker | 9 | 37.4 | (6.92) | 32.3 | (6.71) | −14% | <0.001 |
|  | Fluid infusion | 10 | 33.6 | (5.65) | 42.3 | (6.28) | 26% | <0.001 |

During different intervention, similar changes in cardiac output and systolic displacement obtained by the accelerometer can be seen for most interventions. Hence, Table 1 represents a good correlation between displacement and cardiac output.

Next, in Table 2 below, correlations between changes in cardiac output and changes in the peak systolic values of the acceleration, velocity and displacement are given. The displacement is the change in position during the relevant stage of the heart cycle, here the systole. The changes are not related to a given medical intervention as the point of interest here is to determine whether there is a correlation between the changes in parameters irrespectively of the cause of change.

TABLE 2

| Correlation | n | P-value | Pearson corr. |
|---|---|---|---|
| $\Delta CO$ vs. $\Delta A_{peak,syst}$ | 52 | <0.001 | 0.78 |
| $\Delta CO$ vs. $\Delta V_{peak,syst}$ | 52 | <0.001 | 0.78 |
| $\Delta CO$ vs. $\Delta D_{peak,syst}$ | 52 | <0.001 | 0.57 |

Cardiac output (CO) [L min$^{-1}$];
Peak systolic acceleration ($A_{peak,syst}$) [m sec$^{-2}$];
Peak systolic velocity ($V_{peak,syst}$) [m sec$^{-1}$];
Peak systolic displacement ($D_{peak,syst}$) [mm]

Similarly to Table 2, correlations between changes in stroke volume and changes in the peak systolic values of the acceleration, velocity and displacement are given in Table 3 below.

TABLE 3

| Correlation | n | P-value | corr. |
|---|---|---|---|
| $\Delta SV$ vs. $\Delta A_{peak,syst}$ | 52 | 0.057 | 0.27[1] |
| $\Delta SV$ vs. $\Delta V_{peak,syst}$ | 52 | <0.001 | 0.51 |
| $\Delta SV$ vs. $\Delta D_{peak,syst}$ | 52 | <0.001 | 0.36 |

Stroke volume (SV) [mL].
[1]Spearman correlation, not normally distributed data

Again, similarly to Table 2, correlations between changes in heart rate and changes in the peak systolic values of the acceleration, velocity and displacement are given in Table 4 below.

TABLE 4

| Correlation | n | P-value | corr. |
|---|---|---|---|
| $\Delta HR$ vs. $\Delta A_{peak,syst}$ | 52 | <0.001 | 0.75 |
| $\Delta HR$ vs. $\Delta V_{peak,syst}$ | 52 | <0.001 | 0.66 |
| $\Delta HR$ vs. $\Delta D_{peak,syst}$ | 52 | 0.309 | 0.35 |

Heart rate (HR) [s$^{-1}$]

The best correlation is obtained in relation to cardiac output, second best is the correlation to heart rate, and least in relation to stroke volume. The good correlation to cardiac output is thereby surprising as cardiac output is typically quantified as the product of heart rate and stroke volume. This is a consequence of the complexity of these parameters and the technical difficulties and uncertainties of the present ways of measuring them during surgical procedures.

Figure 14:
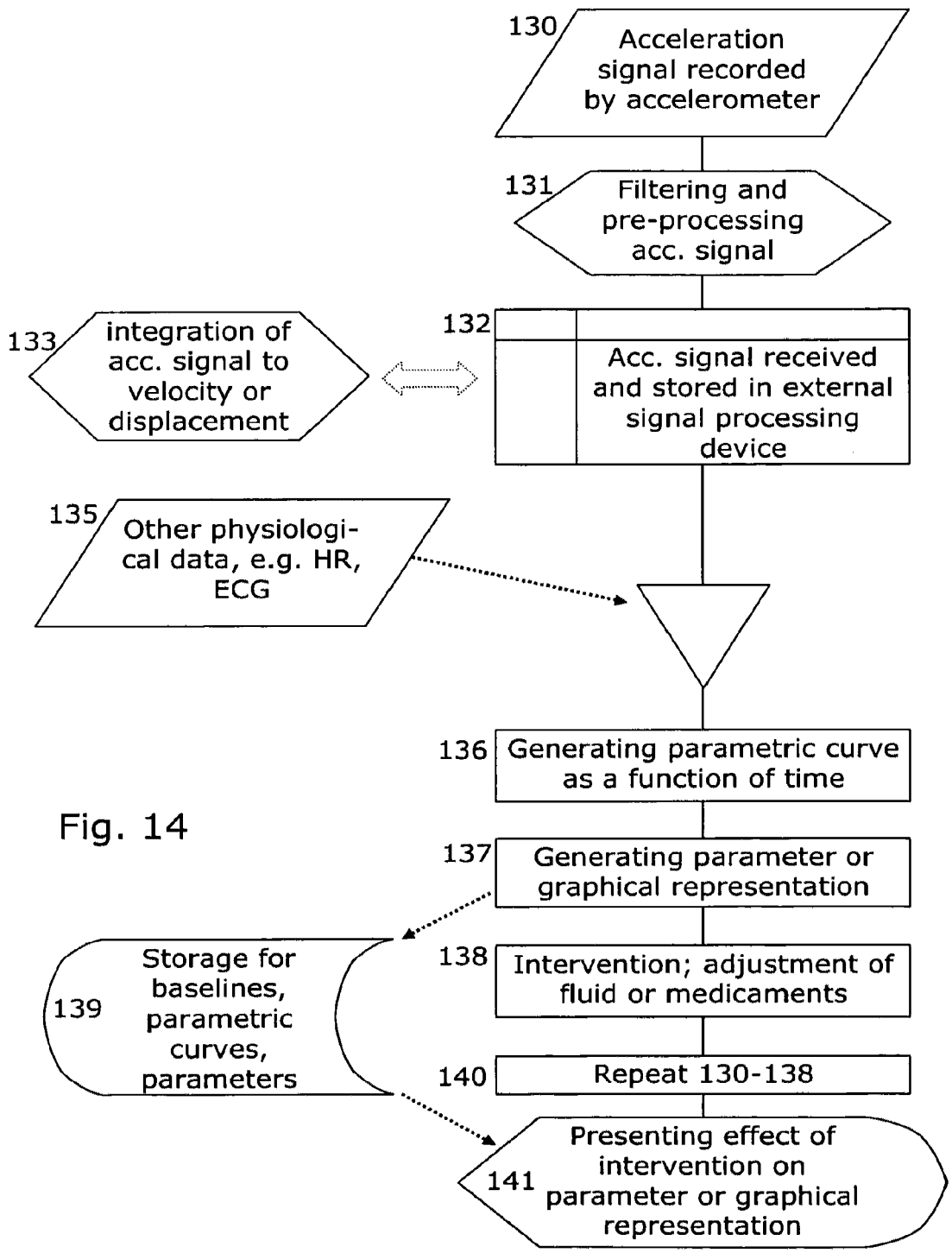
FIGS. 14 and 15 are flow diagrams illustrating the method and system or software architecture according to embodiments of the invention.
Figure 15:
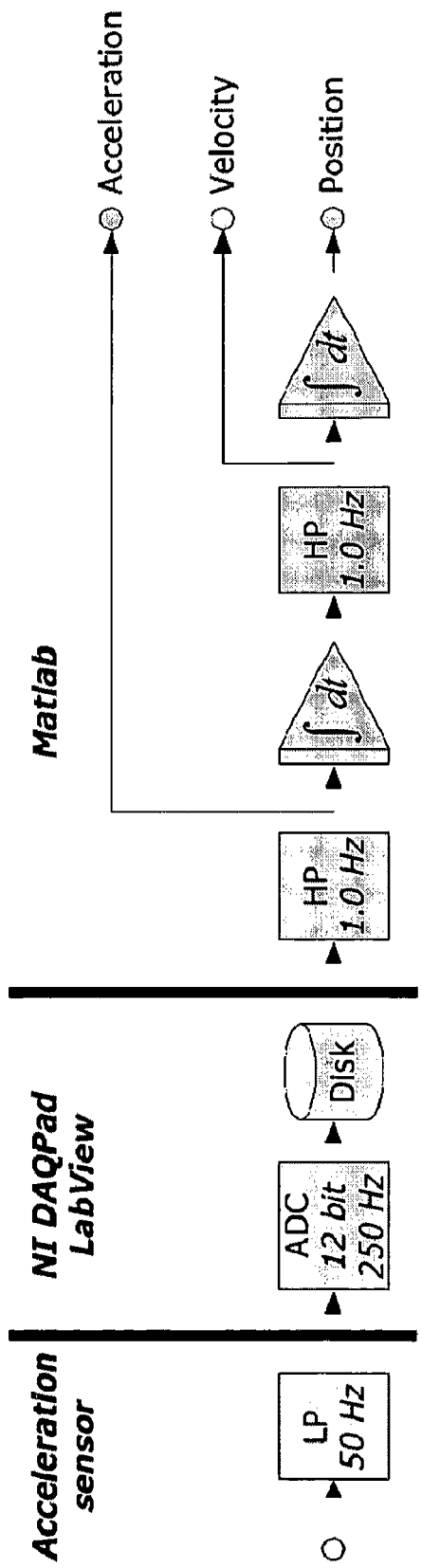

FIGS. 14 and 15 are flow diagrams used in the following to various embodiments of the invention. The flow diagrams outline and exemplify the process steps comprised in the methods according to various embodiments of the invention. The flow diagrams also outline and embody the system architecture, such as software architecture, of the system for estimating changes in cardiac pumping capacity in response to an intervention according to an embodiment of the invention.

The flow diagram of FIG. 14 describes process steps or program modules for the overall process according to various embodiments of the invention, where dotted arrows represent optional elements.

The flow diagram of FIG. 15 illustrates the data processing in relation to the hardware modules in a specific embodiment.

The invention can be implemented by means of hardware, software, firmware or any combination of these. The invention or some of the features thereof can also be implemented as software running on one or more data processors and/or digital signal processors.

In one embodiment, the signal processing unit is incorporated in a post-surgery monitoring unit and the method is performed on the cardiac surgery patient in the hours and days following operation, preferably until at stabilized condition is reached.

The individual elements of an embodiment of the invention may be physically, functionally and logically implemented in any suitable way such as in a single unit, in a plurality of units or as part of separate functional units. The invention may be implemented in a single unit, or be both physically and functionally distributed between different units and processors.

Although the present invention has been described in connection with the specified embodiments, it should not be construed as being in any way limited to the presented examples. The scope of the present invention is to be interpreted in the light of the accompanying claim set. In the context of the claims, the terms "comprising" or "comprises" do not exclude other possible elements or steps. Also, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A system for assisting a decision relating to intravenous administration of medicaments to, or changes in the intravascular volume of, a cardiac surgery patient, the system comprising
- an accelerometer to be positioned on, in or just below an outer surface part of the myocardium in the supply region of the one or more of left anterior descending artery (LAD), circumflex artery (CX) or right coronary artery (RCA) on which the cardiac surgery has been performed, for registering an acceleration signal characteristic to accelerations of said outer surface part(s) as a function of time in three different directions; and
- a signal processing unit comprising:
- a recording module configured to record the registered acceleration signal from the accelerometer;
- a data processing module configured to generate a parameter or a graphical representation based on the obtained acceleration signal, or based on an integrated signal representing velocity or position, the parameter or the graphical representation correlating with cardiac pumping capacity of the patient's heart, the data processing module being configured to generate a parametric curve being a function of time in at least one of:
- a three dimensional graph with axes corresponding to the acceleration, or integrated signals representing relative velocities or positions, in the three different directions, or
- a graph with a first axis corresponding to acceleration, velocity, or position, and a second axis corresponding to correlated pressure from synchronically registered blood pressure;
- a storage medium configured to store of one or more baselines for the parameter or graphical representation generated over a period of time including or following intravenous administration of medicaments or changes in the intravascular volume; and
- a comparison module configured to compare the parameter or graphical representation generated after intravenous administration of medicaments or changes in the intravascular volume with a stored baseline to graphically present a development over time of the parameter or graphical representation, this being useful for evaluating the effect of the intravenous administration of medicaments or change in the intravascular volume and whether this should be continued, halted, or reversed,
- wherein the parametric curve being a function of time is based on an amplitude of the accelerometer signal or an amplitude of an integrated signal representing velocity or position.

2. The system according to claim 1, wherein the data processing software is further configured to correlate the acceleration signal, or integrated signals representing relative velocities or positions, with electrocardiogram and/or blood pressure to assign segments of the parametric curve to stages of the cardiac cycle and determine the length of one or more of said segments as a parameter or graphical representation which correlates with cardiac pumping capacity.

3. The system according to claim 1, wherein the accelerometer is incorporated in a pacemaker electrode, and wherein the signal processing unit is incorporated in a post-surgery monitoring unit.

4. The system according to claim 1, wherein the parametric curve is a loop configured to generate new parameters according to an area encircled by the loop.

* * * * *